US006999183B2

(12) United States Patent
Nielsen et al.

(10) Patent No.: US 6,999,183 B2
(45) Date of Patent: Feb. 14, 2006

(54) DETECTION SYSTEM FOR NANOMETER SCALE TOPOGRAPHIC MEASUREMENTS OF REFLECTIVE SURFACES

(75) Inventors: Henrik K. Nielsen, San Jose, CA (US);
Lionel Kuhlmann, San Jose, CA (US);
Mark Nokes, Palo Alto, CA (US)

(73) Assignee: KLA-Tencor Corporation, San Jose, CA (US)

( * ) Notice: Subject to any disclaimer, the term of this patent is extended or adjusted under 35 U.S.C. 154(b) by 1227 days.

(21) Appl. No.: 09/195,533

(22) Filed: Nov. 18, 1998

(65) Prior Publication Data

US 2001/0013936 A1    Aug. 16, 2001

(51) Int. Cl.
G01B 11/30    (2006.01)
(52) U.S. Cl. .................................... 356/612
(58) Field of Classification Search .............. 356/371, 356/600, 612, 613; 250/208.2
See application file for complete search history.

(56) References Cited

U.S. PATENT DOCUMENTS

| 3,866,038 | A | * | 2/1975 | Korth .......................... 356/371 |
| 3,885,875 | A | * | 5/1975 | Rosenfeld et al. .......... 356/371 |
| 4,732,473 | A | | 3/1988 | Bille et al. |
| 5,015,096 | A | * | 5/1991 | Kowalski et al. ........... 356/371 |
| 5,118,955 | A | | 6/1992 | Cheng |
| 5,134,303 | A | | 7/1992 | Blech et al. |
| 5,164,579 | A | * | 11/1992 | Pryor et al. ............... 250/208.2 |
| 5,233,201 | A | | 8/1993 | Cheng |
| 5,248,889 | A | | 9/1993 | Blech et al. |
| 5,270,560 | A | | 12/1993 | Cheng |
| 5,379,150 | A | | 1/1995 | Miyazaki et al. |
| 5,452,078 | A | | 9/1995 | Cheng |
| 5,523,582 | A | | 6/1996 | Cheng |
| 5,596,406 | A | | 1/1997 | Rosencwaig et al. |
| 5,764,363 | A | | 6/1998 | Ooki et al. |
| 5,798,829 | A | | 8/1998 | Vaez-Iravani |
| 5,812,266 | A | * | 9/1998 | Hercher ....................... 356/371 |

(Continued)

FOREIGN PATENT DOCUMENTS

DE    15281989    2/1997

(Continued)

OTHER PUBLICATIONS

"YIS-200SP-4 Magic Mirror", HOLOGENIX, [Online] XP002132557, retrieved from the Internet Mar. 7, 2000, website: http://semiconductor.supersites.net/semin2/hologenix/pageb1.htm.

(Continued)

Primary Examiner—Richard A. Rosenberger
(74) Attorney, Agent, or Firm—Smyrski Law Group, A P.C.

(57) ABSTRACT

A linear position array detector system is provided which imparts light energy to a surface of a specimen, such as a semiconductor wafer, receives light energy from the specimen surface and monitors deviation of the retro or reflected beam from that expected to map the contours on the specimen surface. The retro beam will, with ideal optical alignment, return along the same path as the incident beam if and only if the surface is normal to the beam. The system has a measurement device or sensor within the path of the retro or reflected beam to measure deviation of the retro beam from expected. The sensor is preferably a multiple element array of detector-diodes aligned in a linear fashion. A unique weighting and summing scheme is provided which increases the mechanical dynamic range while preserving sensitivity. The system further includes a bright field Nomarski Differential Interference Contrast sensor used to split the beam into two beams and for scanning in an orientation orthogonal to the orientation of the optical lever created by the system.

40 Claims, 8 Drawing Sheets

U.S. PATENT DOCUMENTS 5,841,127 A * 11/1998 Throngnumchai ....... 250/208.2

FOREIGN PATENT DOCUMENTS

| EP | 0350595 | 1/1990 |
| EP | 0568478 | 11/1993 |
| JP | 06222013 | 12/1994 |
| WO | 9825131 | 6/1998 |

OTHER PUBLICATIONS

Optics Glossary, [Online] XP-002132518, retrieved from the Internet on Mar. 8, 2000, website: http://www.om.tu-harburg.de/re/glossary.htm.; "Optical Isolator".

* cited by examiner

DETECTION SYSTEM FOR NANOMETER SCALE TOPOGRAPHIC MEASUREMENTS OF REFLECTIVE SURFACES

BACKGROUND OF THE INVENTION

1. Field of the Invention

The present invention relates generally to the art of optical inspection of specimens, such as semiconductor wafers and hard disk surfaces, and more specifically to a system for determining surface topographies in the nanometer range using optical techniques.

2. Description of the Related Art

Optical inspection techniques for specimens, such as semiconductor wafers, have assessed the relative flatness of specimen surfaces using various techniques. Surface flatness is a critical parameter used to determine the overall quality of a semiconductor wafer, and wafers having large irregular areas or small areas with radical height differences are undesirable.

Current tools available to measure wafer surface flatness include the "Magic Mirror" tool by Hologenix. The "Magic Mirror" operates by directing collimated light toward the wafer surface, wherein the collimated light source is angularly displaced from the wafer surface. The "Magic Mirror" system subsequently receives the reflected light. Light may be scattered toward or away from the detector. The "Magic Mirror" thereupon produces a two dimensional depiction of the surface of the observed semiconductor wafer, with associated light and/or dark areas depending on the type of defect. As can be appreciated, the "Magic Mirror" is a very subjective method of detecting surface contours. With different types of defects producing different optical effects, one cannot say for certain what type or size of defect is responsible for the bright or dark spot or area in the "Magic Mirror" depiction. Hence algorithms cannot conclusively provide areas of concern or threshold exceedance with reasonable degrees of certainty. The final two dimensional representation obtained from the "Magic Mirror" must be studied by an operator, and results depend on many uncontrollable factors.

An alternate method for measuring surface contours utilizes a profiler, much like a stylus on a record player, which directly contacts the semiconductor wafer surface. Such a system moves the semiconductor wafer and sensor relative to each other causing the sensor to linearly translate across the surface, thereby providing contact between the profiler and the entire surface. Movement of the profiler is recorded, and surface irregularities are detected when the profiler deflects beyond a threshold distance. The problems inherent in a profiler are at least twofold: first, a mechanical profiler contacting the wafer surface may itself produce surface irregularities beyond those present prior to the testing, and second, the time required to make accurate assessments of surface irregularities is extensive. For example, a full map of a single 200 mm wafer using a profiler may take between four and twelve hours.

A system is needed which diminishes the time required to perform surface scanning for contour differences and does not have the drawbacks inherent in previously known systems. In particular, it would be desirable to have a system for determining contours in the nanometer range which would not risk damage to the specimen surface and would be quantitative in nature, thereby allowing for computational determination of surface irregularities using threshholding without ad hoc human review.

It is therefore an object of the current invention to provide a system for determining the contours of the surface of a specimen, such as a semiconductor wafer, in the nanometer range which can perform surface irregularity determination in less time than systems previously known.

It is a further object of the current invention to provide a system for determining the contours of the surface of the wafer which does not include non-quantitative measurement techniques.

It is a further object of the current invention to provide a system for determining the contours of a wafer surface which does not increase the risk of damaging the wafer surface.

SUMMARY OF THE INVENTION

According to the present invention, there is provided a linear position array detector system which imparts light energy in a substantially normal orientation to a surface of a specimen, such as a semiconductor wafer, receives light energy from the specimen surface and monitors deviation of the retro beam from that expected.

In accordance with the current invention, a laser, such as an argon ion laser, emits a beam toward an optical isolator, which prevents the retro-beam from entering back into the laser, thereby causing laser instability. The beam is thereupon directed through a series of focusing optics and mirrors onto the surface of the specimen. Optionally, the beam may be caused to pass through polarization optics and a birefringent prism, which produces two beams of orthogonal polarization that diverge from each other by a small angle. This angular divergence results in a physical separation of the two beams at the focus of the optical system on the specimen surface, in the same manner as that used in Nomarski differential interference contrast (DIC) microscopy. DIC microscopy is illustrated in U.S. Pat. No. 5,798,829 to Mehdi Vaez-Iravani, entitled "Single Laser Bright Field and Dark Field System for Detecting Anomalies of a Sample", issued Aug. 25, 1998 and assigned to KLA-Tencor Corporation.

After the split beam contacts the specimen surface, the light scattered at a narrow angle to the incident beam from surface defects is collected in the Dark Field Narrow (DFN) channel, while most of the light scattered at larger angles by the surface defects is collected in the Dark Field Wide (DFW) channel. The remainder of the beam is specularly reflected back through the components outlined above. As two beams illuminate the wafer surface, two beams are returned through the elements up to the birefringent prism, which combines the two retro beams into a single beam. The single beam is returned through the remaining elements.

The retro beam will, with ideal optical alignment, return along the same path as the incident beam if and only if the surface is normal to the beam. The current invention provides a measurement device or sensor within the path of the retro beam to measure deviation of the retro beam from expected. The system uses a diode/detector array, which is preferably a multiple element array of detector-diodes aligned in a linear fashion. The system could be implemented using a CCD sensor or other sensor, but these devices have certain drawbacks. The diode/detector array can be positioned proximate the optical isolator to receive the retro beam, or alternately a polarizing or non-polarizing beamsplitter may be employed in the retro path to divert the retro beam. The beam wander results in the retro beam illuminating different diodes in the array. Weighting the signal from each detector with a weight proportional to the relative position of the beam and adding signals from all detectors in conjunction with a signal normalization using the total detected light power provides a linear voltage proportional to the beam position independent of the absolute light power level.

The preferred diode/detector array is made up of 76 adjacent detector elements each having the ability to have electrical connections at exposed ends of the element. Each diode has a 280 micrometer length with 30 micrometers between elements. The entire mechanical dynamic range of the array in this longest direction is 23.56 millimeters. The width of these elements is 6.35 millimeters, and thus mechanical alignment is non-critical for a one millimeter diameter beam. The beam in the present arrangement, as described in more detail below, is 22 micrometers by 50 or 340 micrometers at the focal point on the specimen, but 1 mm in diameter at the detector. It may be appreciated by those of ordinary skill in the art that diode arrays having different sizing or composition of elements may be employed while still within the scope of the current invention.

The system measures output from each of the 76 elements in the array and calculates the center of mass for the entire arrangement. The relative power of the beam being Gaussian dictates that the arrays be sized such that the expected beamwidth spans several array elements, including spanning two, three, or more array elements. The system operates by scanning the wafer and monitoring movement of the retro beam from expected. In operation, the present desing may offer an ability to detect surface variations of less than approximately 1000 nanometers and surface contours over areas larger than particles or scratches.

Each diode detector in the 76 element diode/detector array uses a pre-amplifier. To preserve sensitivity, the preamplifier gain must be relatively high, which is undesirable. Thus the invention further includes a scheme to increase the mechanical dynamic range while preserving sensitivity.

The signals from each individual diode are summed using a conventional inverting sum amplifier. Weighting resistors 1 through n provide resistances R, 3*R, through [(2*n)−1]*R, thereby providing weighting of the signals received from the sensor array. One summing amplifier is used for each group of amplifiers, wherein each group has 5 amplifiers and accordingly 5 array elements. The optimal number of diodes to be grouped together depends on the laser beam width, diode size, and the gap between the diodes. The system determines the position signal by subtracting the values from two neighbor groups of diodes from one another. A unique stair-stepping arrangement of weightings is employed in the current invention to provide linear response, preserve the dynamic range over the expected path of the retro beam, and prevent saturation of the signal.

Data are selectively passed from the signal groups 1 through n using a multiplexer which receives a digital signal from programmable array logic based on a threshholding arrangement.

This detector as described senses deviations of the specimen surface orientation from normal to the beam along one axis; deviations along the orthogonal axis may be sensed using the optional Nomarski DIC channel by appropriate orientation of the birefringent prism and polarizing optics. Other objects, features, and advantages of the present invention will become more apparent from a consideration of the following detailed description and from the accompanying drawings.

DETAILED DESCRIPTION OF THE INVENTION

Figure 1:
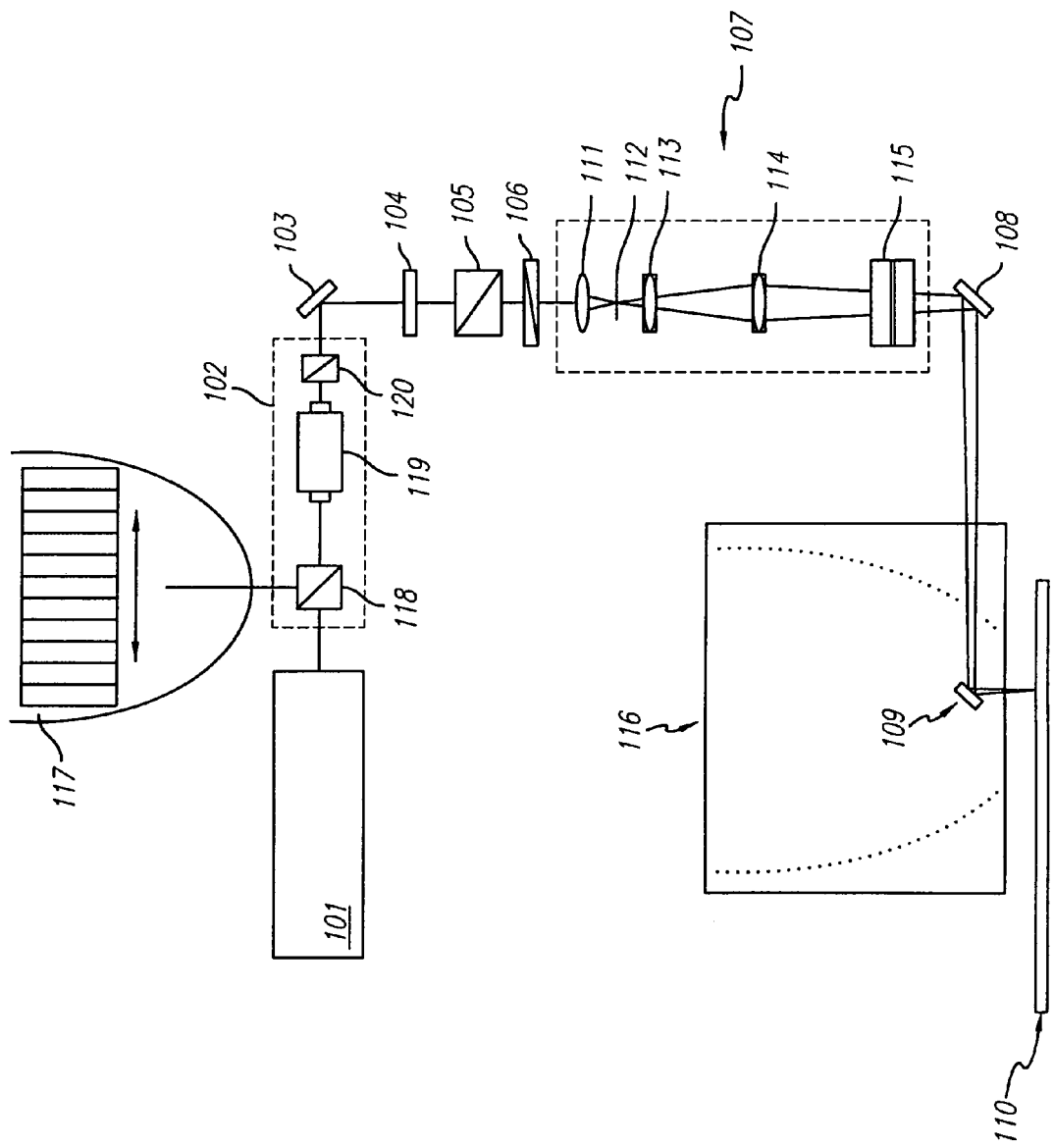
FIG. 1 illustrates the preferred embodiment of the inventive linear position array detector system having a sensor receiving a signal diverted from the input polarizer of the optical isolator.

FIG. 1 illustrates the inventive linear position array detector system. The system may be modified from existing technology, such as the existing SP1 system manufactured by KLA-Tencor Corporation of San Jose, Calif. The SP1 system may include Stationary Beam Illumination technology and an optional Bright Field scanning Nomarski Differential Interference Contrast sensor.

From FIG. 1, a laser 101, such as an argon ion laser operating at a wavelength of 488 nm, emits a laser beam toward an optical isolator 102. The optical isolator comprises an input polarizer 118, a Faraday effect polarization rotator 119, and an output polarizer 120, and operates to rotate the polarization of any beam passing through it by 45 degrees from its incident polarization. The polarizers are oriented to pass the outgoing linearly polarized beam from the laser. The retro beam's polarization will be normal to the pass direction of input polarizer 118 after passing through the Faraday cell 119, however, and will thereby be attenuated before it enters the laser cavity and causes instability. The beam is thereupon directed toward a mirror 103 and down through a half wave plate 104. The beam may optionally be directed through a polarizing beamsplitter 105, discussed below, and toward a birefringent, or DIC (differential interference contrast), prism 106. The DIC prism 106 operates to split the incoming linearly polarized beam into two separate beams of orthogonal linear polarization that diverge from each other by a small angle. These two beams then pass through an optics arrangement 107, which comprises a series of lenses used to focus the beams toward the wafer surface. The focused beams are directed to second mirror element 108, which directs the beam toward third mirror element 109 and onto the surface of the wafer 110. As shown herein, the beam is stationary as opposed to scanning beams used in other known optical inspection devices.

The optics arrangement 107 includes first lens 111, mask 112, second lens 113, third lens 114, and fourth and fifth lens combination 115, comprising fourth lens 115*a* and fifth lens 115*b*. These lenses in the optics arrangement 107 shape and focus the light beams to fix at a desired spot size on the surface of the wafer 110. Dark Field Collection arrangement 116 is used in conjunction with Dark Field Narrow and Dark Field Wide channels.

As illustrated in FIG. 1, the stationary laser beam intercepts the wafer surface at normal incidence. After the split beam contacts the wafer surface it is reflected back through the components shown, particularly onto third mirror element 109, second mirror element 108, optics arrangement 107, DIC prism 106, polarizing beamsplitter 105, half wave plate 104, first mirror element 103, and optical isolator 102. Again, two beams illuminate the wafer surface, and two beams are thus returned to third mirror element 109, second mirror element 108, optics arrangement 107, and to DIC prism 106. DIC prism 106 combines the two retro beams into a single beam, which is returned through the remaining elements illustrated and toward laser 101. The optical isolator 102 attenuates the beam significantly by orthogonal polarization rejection at polarizers 120 and 118, respectively.

While the system disclosed herein illustrates a normal application of a beam to the specimen 110, it is to be understood that the teachings of the current invention contemplate application of a beam to a specimen in non-normal or oblique angles. As used herein, the term "retro" or "retro beam" is intended to cover both normal and non-normal reflection of the beam from the specimen, and therefore may include darkfield or brightfield techniques.

In the mechanization of FIG. 1, after the split beam contacts the specimen surface, the light scattered at a narrow angle to the incident beam from surface defects is collected in the Dark Field Narrow (DFN) channel, while most of the light scattered at larger angles by the surface defects is collected in the Dark Field Wide (DFW) channel. The remainder of the beam is specularly reflected back through the components outlined above. As two beams illuminate the wafer surface, two beams are returned through the elements up to the birefringent prism, which combines the two retro beams into a single beam. The single beam is returned through the remaining elements. This mechanization therefore forms a darkfield collection arrangement in the embodiment shown.

Portions of the current system resemble the system disclosed in pending U.S. patent application Ser. No. 08/933,771 to Mehdi Vaez-Iravani et al., filed Sep. 19, 1997 and assigned to KLA-Tencor Corporation, the entirety of which is incorporated herein by reference.

In the configuration illustrated for the invention disclosed herein, two spot sizes have been successfully employed to perform the tasks described herein. One spot size is a 22 micron by 50 micron spot, while the other is a 22 micron by 340 micron spot. The spot size used is selected by using either lens 113 or lens 114. As may be appreciated by those of skill in the art, the larger spot size provides a higher throughput but has a tendency to produce lower quality scans, as lower power applied to the surface of the wafer yields less sensitivity. As disclosed herein, various spot sizes may be employed successfully with this invention, including the two disclosed herein, while still within the scope of the invention. Generally speaking, a larger spot size will yield less sensitivity and greater throughput while a smaller spot size will produce greater sensitivity but take longer to complete a scan.

The retro beam will, with ideal optical alignment, return along the same path as the incident beam if and only if the surface is normal to the beam. With this knowledge, a measurement device or sensor can be located within the path illustrated in FIG. 1 to measure deviation of the retro beam from the transmitted beam.

Figure 2:
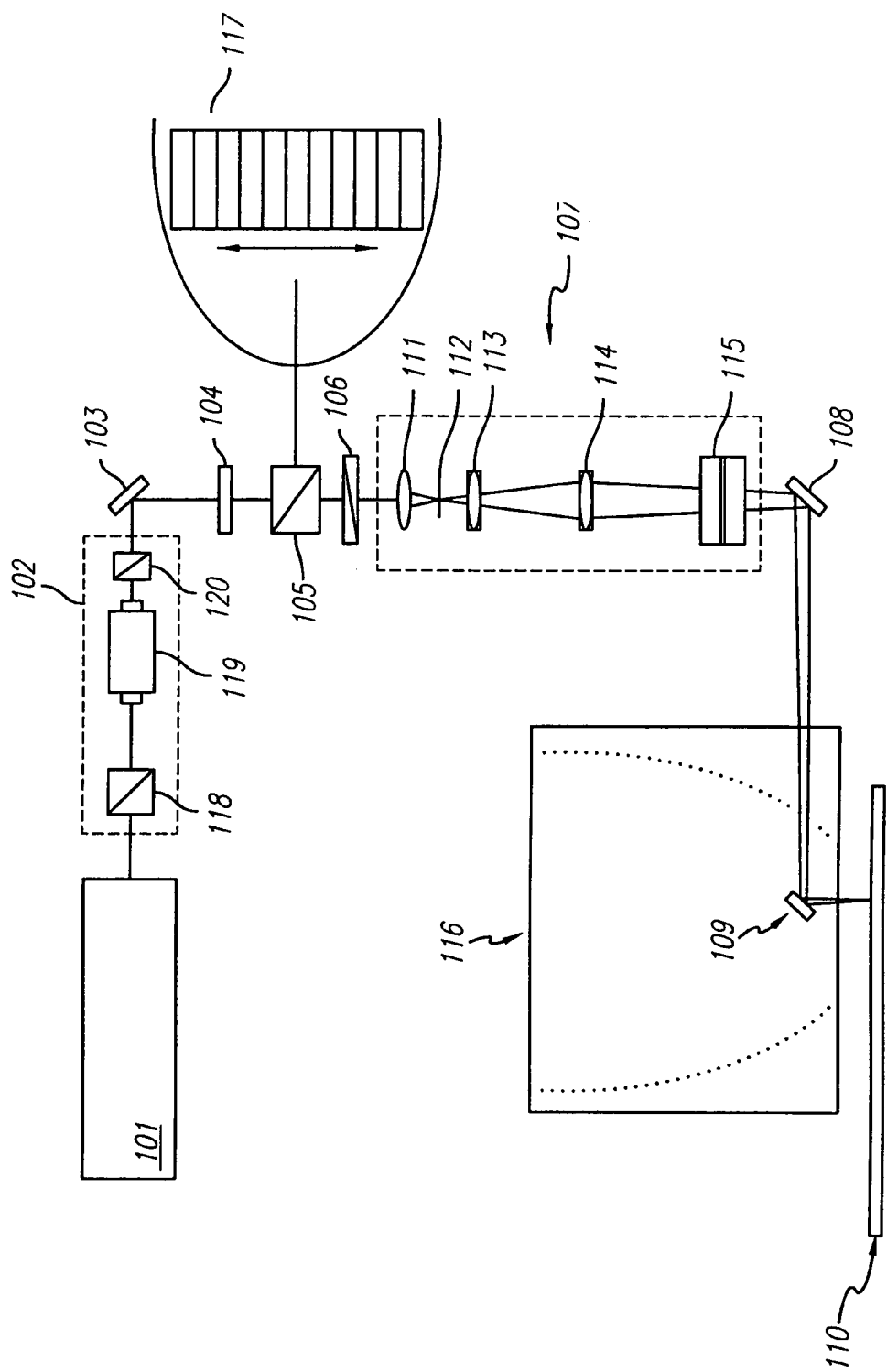
FIG. 2 is an alternate embodiment of the invention having a sensor receiving a signal diverted from a point within the optical elements using a polarizing or non-polarizing beam-splitter.

The current system provides the ability to perform a deviation measurement using the bright field scanning Nomarski Differential Interference Contrast sensor 106. The bright field scanning Nomarski Differential Interference Contrast sensor 106 splits the beam into two separate beams which are applied to the surface of the specimen 110 as shown in FIGS. 1 and 2 and outlined above. The specimen 110 is rotated about a vertical axis and concurrently translated horizontally during a typical scan while the beam remains stationary. As a result of the scanning process, the Nomarski DIC sensor 106 senses occurrences in a predetermined direction, such as in a tangential direction from the center of the specimen, while the optical lever created by the optics senses occurrences in an orthogonal direction to that of the Nomarski DIC sensor 106. While the system may use the Nomarski DIC sensor 106 to measure in the tangential direction and the optical lever to measure in the radial direction, it is to be understood that other orientations are possible but it is preferred that the Nomarski DIC sensor and optical lever are always orthogonal to one another.

FIG. 1 illustrates one embodiment of the system with a diode/detector array 117 receiving the retro beam from the isolator's input polarizer 118. While the diode/detector array, as will be described below, is preferably a multiple element array of detector-diodes, the system could be implemented alternately using a CCD sensor, which has certain drawbacks. The system illustrated in FIG. 2 presents an alternate positioning of the diode/detector array 117. The diode/detector array 117 in FIG. 1 is positioned proximate the optical isolator 102 to divert the retro beam using input polarizer 118. Alternately, the diode detector/array 117 may be positioned just before the DIC prism in the incident path such that the polarizing beamsplitter 105 diverts the retro beam toward the detector array, as illustrated in FIG. 2. In either condition, the retro beam is deflected from the path toward the diode/detector array, and any deviation from normal constitutes a local wafer surface irregularity. The beam wander results in the retro beam illuminating different diodes in the array, discussed below. Weighting the signal from each detector with a weight proportional to the relative position of the beam and adding signals from all detectors in conjunction with a signal normalization using the total detected light power provides a linear voltage proportional to the beam position independent of the absolute light power level. The system measures the summed diode signal and at the same time records the (x,y) or (r,Θ) position on the wafer and generates a map of relative surface slopes. The integrated signal of the slope map produces a surface topography or surface height map.

Figure 3:
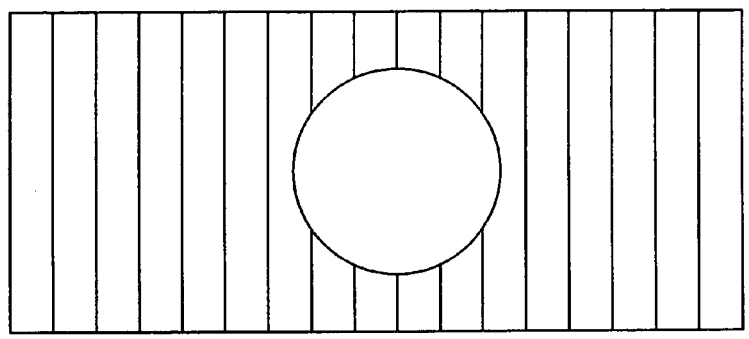
FIG. 3 presents a detector array in accordance with the teachings of the present invention having a beam imparted thereon.

A sample detector array having a beam imparted thereon is illustrated in FIG. 3. The diode/detector array 117 is made up of 76 adjacent detector elements each having the ability to have electrical connections at exposed ends of the element. Different sized arrays may be employed while still within the scope of the current invention; however, as discussed below, large two-dimensional blocks of detectors have speed and size/sensitivity concerns which are undesirable. The overall diode/detector array 117 includes 76 diodes, each diode having a 280 micrometer length with 30 micrometers between elements. The entire mechanical dynamic range of the array in this longest direction is 23.56 millimeters. The width of these elements is 6.35 millimeters, and thus mechanical alignment is non-critical for a one millimeter diameter beam.

According to the arrangement presented in FIGS. 1 and 2 in conjunction with the diode/detector array 117 illustrated, the system measures output from each of the 76 elements in the array and calculates the center of mass for the entire arrangement, normalized with the total detected light power.

Figure 4:
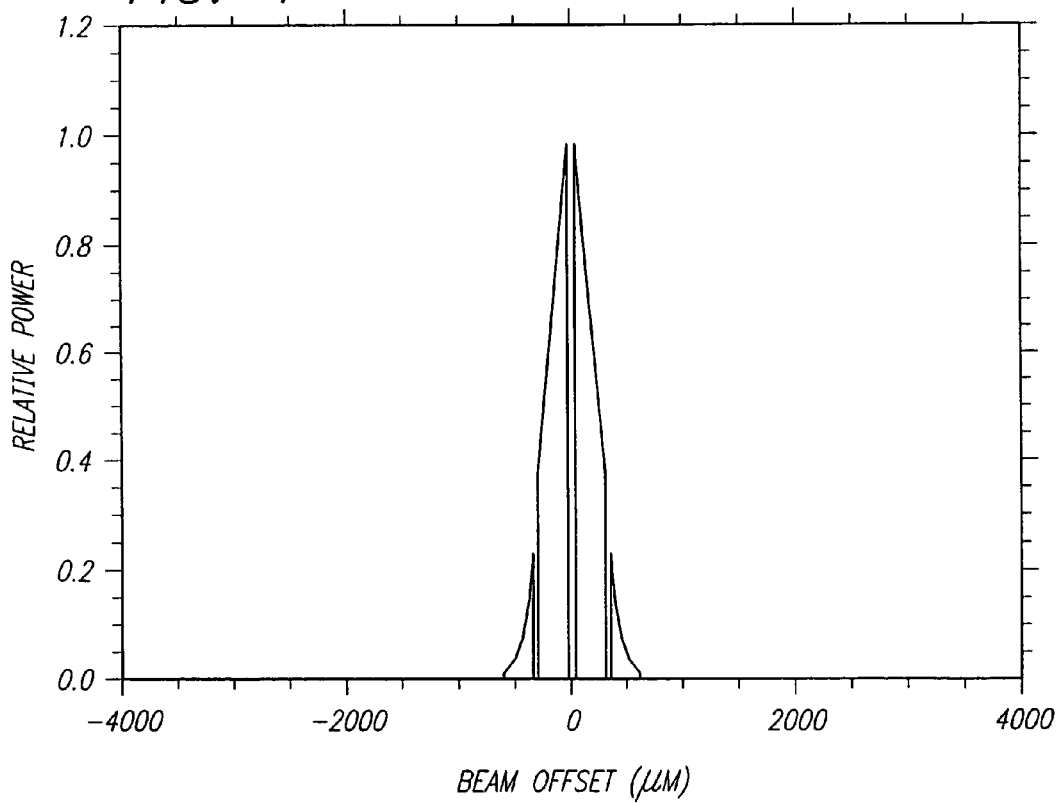
FIG. 4 illustrates the relative power of a signal imparted on the diode/detector array of FIG. 3.

From FIG. 3, the beam is nominally positioned at a predetermined location in the retro beam path when the system according to FIG. 1 or 2 is operating. The relative power of the beam is Gaussian, as shown in FIG. 4. The arrays are preferably sized such that the expected beamwidth spans several array elements, and as shown in FIG. 3, the beam spans six elements of the array. The arrangement shown preserves the sensitivity of the system over a larger mechanical dynamic range than, for example, a bi-cell wherein the beam strikes two cells in the two cell array. The system operates by scanning the wafer and monitoring the movement of the retro beam from the nominal value in the sensor array arrangement shown in FIG. 3. Typical beam deflection in the FIG. 3 arrangement is right to left, meaning that the beam will typically travel right or left in the presence of anomalies on the wafer surface.

Figure 5:
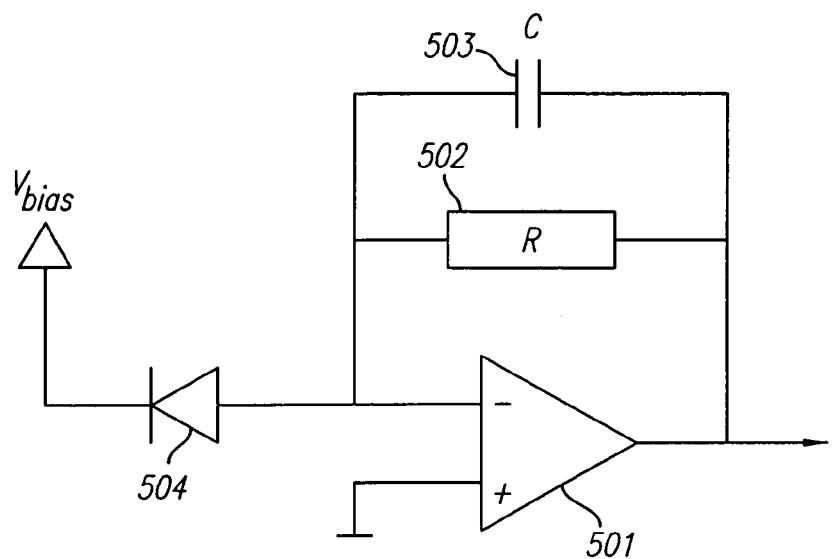
FIG. 5 is the diode/pre-amplifier circuit used with each element of the diode/detector array.

Each diode detector in the 76 element diode/detector array 117 operates with a pre-amplifier as shown in FIG. 5. The pre-amplifier is configured as a conventional transconductance amplifier having low pass filtering. Amplifier 501 has resistor 502 and capacitor 503 connected in parallel therewith in a feedback orientation. Diode 504 represents one of the 76 diodes in the array. Each diode, such as diode 504 of FIG. 5, operates in a photo-conductive mode, or in other words operates with a bias voltage. The feedback resistor 502 determines the gain of the amplifier, while the resistor and the capacitor act as a single pole low pass filter having a time constant equal to RC. This provides a −3 dB cutoff frequency.

In order to preserve sensitivity for the arrangement shown, the pre-amplifier gain must be relatively high. High preamplifier gain results in an increased position signal which can be too large for an analog to digital converter. Thus the configuration shown requires a scheme to increase the mechanical dynamic range while preserving sensitivity, which can be on the order of less than 0.000001 rad for the system illustrated.

Figure 6:
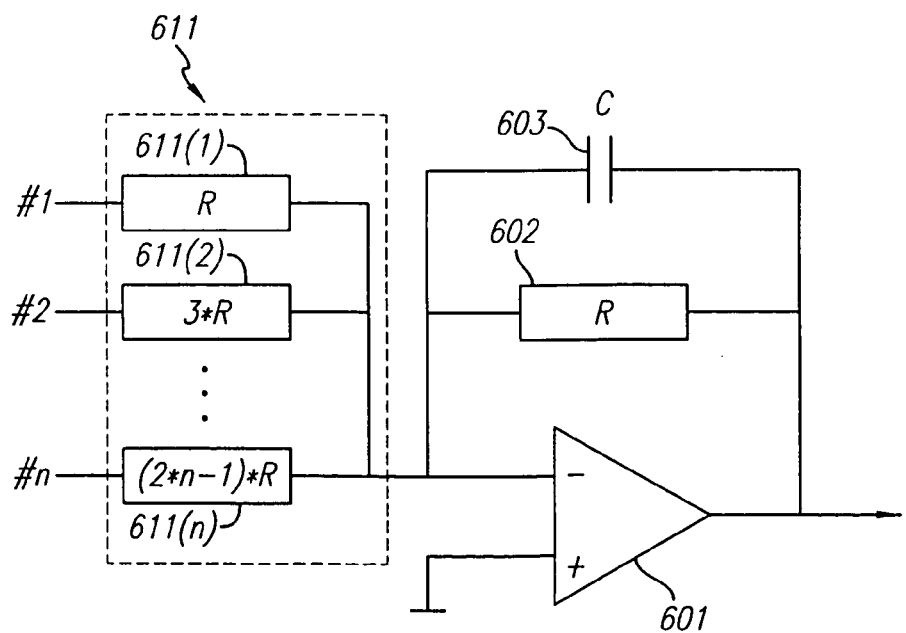
FIG. 6 presents the unique weighting/summing scheme and associated amplifier arrangement employed in accordance with the teachings of the current invention.
Figure 7:
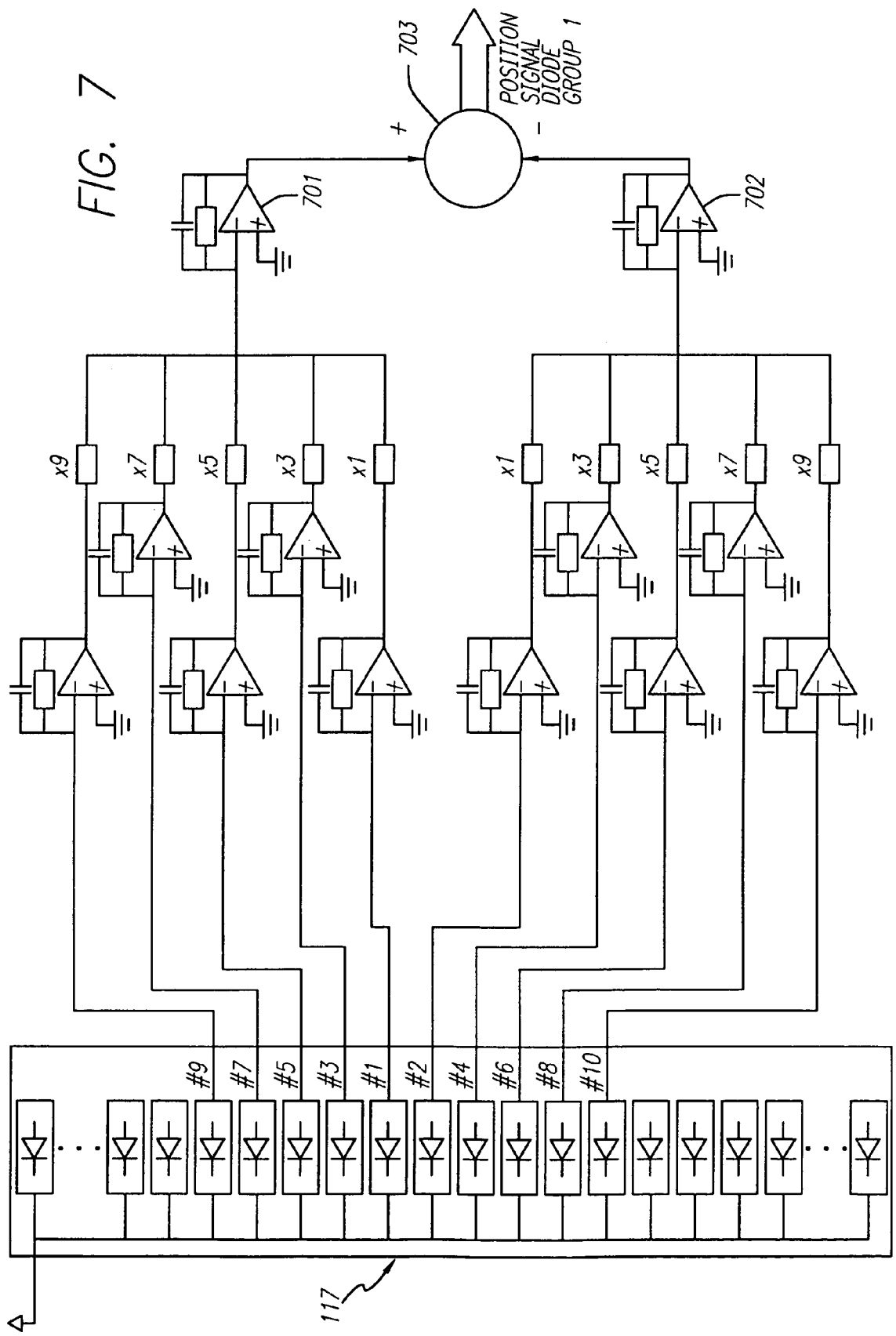
FIG. 7 shows the weighted summing amplifier, preamplifiers, and diode/detectors used in summing the weighted signals from the 10 centermost diodes in the diode/detector array.

The signals from each individual diode are summed as shown in FIG. 6 using a conventional inverting sum amplifier. From FIG. 6, the weighted summing amplifier includes amplifier 601, parallel feedback resistor 602, and parallel capacitor 603. Weighting resistors 611, individually denoted 1 through n, are of resistances R, 3*R, through [(2*n)−1]*R, thereby providing weighting of the signals received from the sensor array. Weighting provides a skewing of information based on the position of the beam; for a beam which is further away than expected, the signal returned from the arrangement of FIG. 6 and subsequent drawings is larger than that of a beam which is only slightly off center. One summing amplifier is used for each group of amplifiers as shown in FIG. 7, wherein each group has five amplifiers and accordingly five array elements. The optimal number of diodes to be grouped together depends on the laser beam width, diode size, and the gap between the diodes. The system determines the position signal by subtracting the values from two neighbor groups of diodes from one another; for example, from FIG. 7, each element in the array has a diode associated therewith along with a preamplifier in accordance with FIG. 5. Each preamplifier has a weight associated therewith, and as shown in FIG. 7, the center elements are numbered 1 and 2, are each attached to preamplifiers, and are weighted with a value of 1. The outermost elements are numbered 9 and 10 and have diodes associated therewith, as well as preamplifiers as in FIG. 5. The outermost elements have weights of 9 associated therewith. Thus the summing amplifiers 701 and 702 receive the weighted signals and compare them in summation element 703. The result of this comparison is the position signal for this diode group of 10 diodes, which is then compared with position signals from other groups of 10 diodes.

Figure 8:
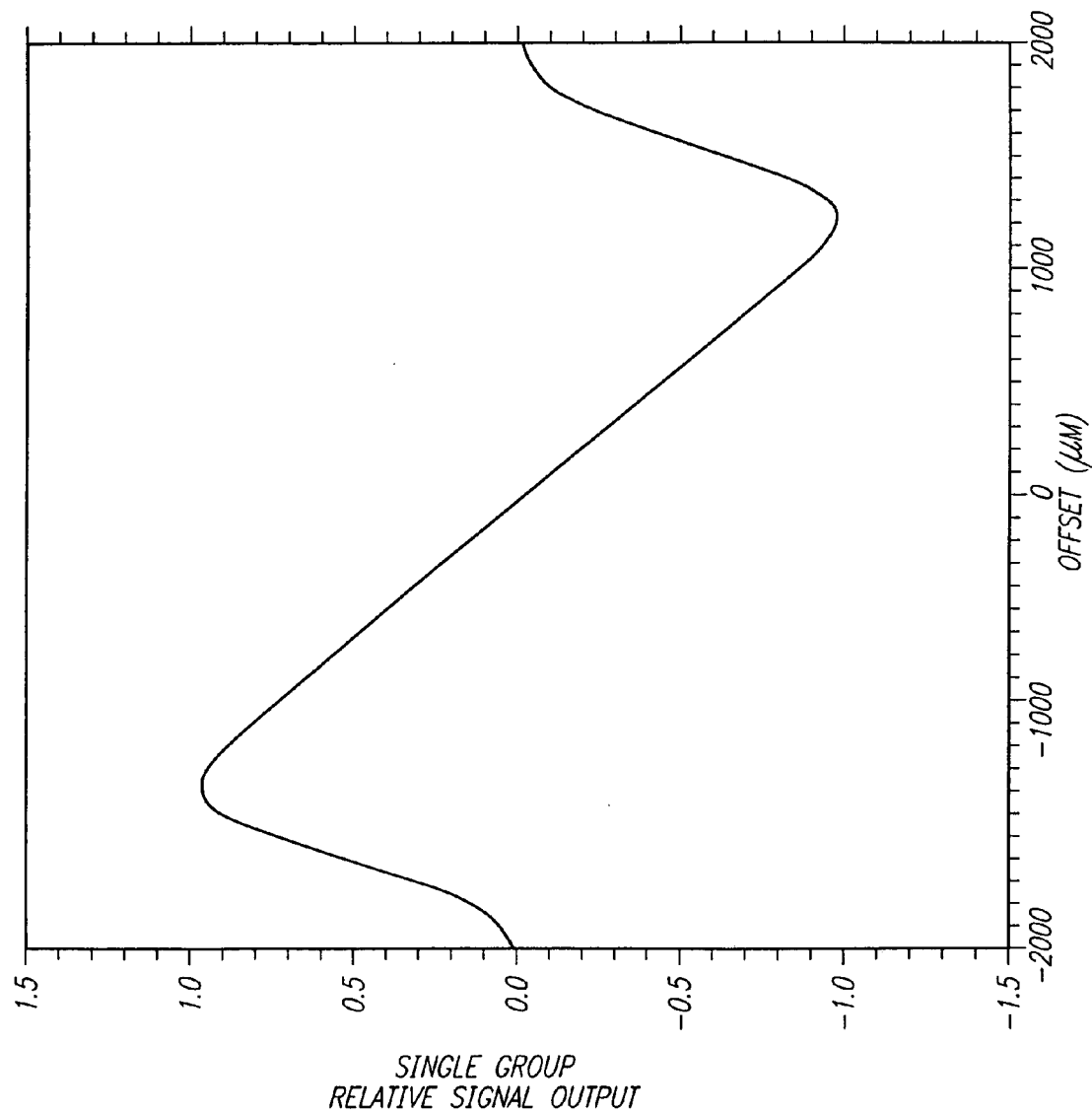
FIG. 8 illustrates the signal from the center group of diodes using the unique weighting scheme of the current invention.

The center group illustrated in FIG. 7 outputs a signal relative to the beam offset as shown in FIG. 8. Nominal beam offset provides a minimal return, out to an approximately 1200 micrometer offset which produces a relative return of ±1.0.

Figure 9:
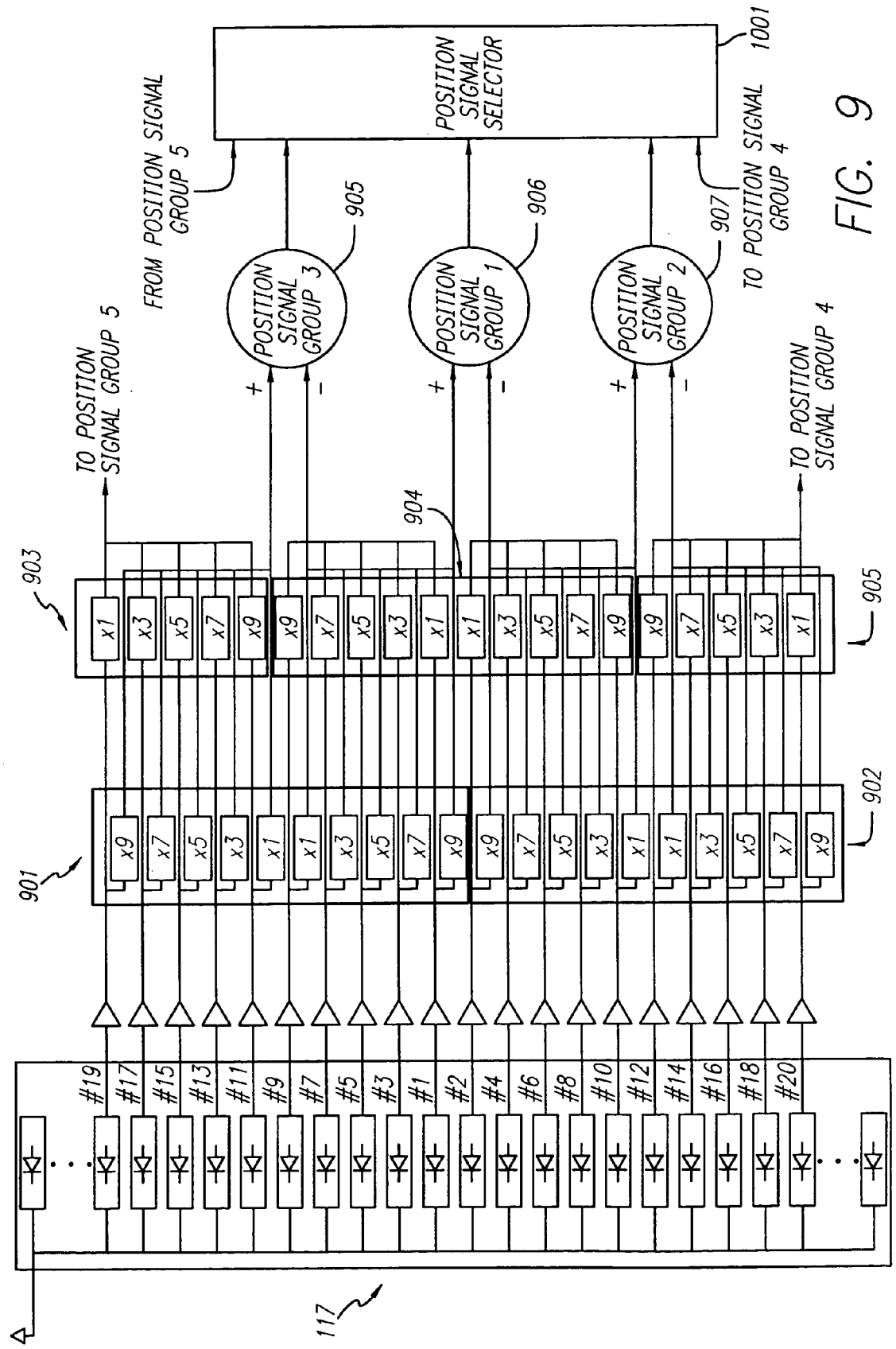
FIG. 9 is a diagram of the stair-stepping dual-weighting arrangement of the current invention, including three summing elements and a position signal selector.

FIG. 9 illustrates the stair-stepping arrangement of weightings used in accordance with the current invention for the 76 diode/array element arrangement of FIG. 3. As shown herein, 20 of the 76 diodes or array elements of the diode/detector array 117 each are connected to resistors, or weighting elements, which provide weighting according to relative position. For example, diode/array element 1 is multiplied by 9 in weighting resistor group 901 and also by 1 in weighting resistor group 904. Diode/array element 2 is multiplied by 9 in weighting resistor group 902 as well as by 1 in weighting resistor group 904. This stair-stepping dual-weighting arrangement permits a relatively linear response across the diode/detector array 117 by essentially mixing weights of adjacent resistors and not overweighting or underweighting areas of the diode/detector array 117, while concurrently providing significant signal deviation upon slight beam movement. The arrangement shown prevents saturation of the signal and preserves the dynamic range over the expected path of the retro beam. From FIG. 9, elements 1, 3, 5, 7, . . . 19 are weighted in weighting resistor group 901, with elements 9 and 11 each receiving weight 1 and elements 1 and 19 receiving weight 9. These elements are summed in position signal group 3 summing element 906. Simultaneously, elements 1, 3, 5, 7, and 9 are weighted with elements 2, 4, 6, 8, and 10 in weighting resistor group 904, thereby avoiding overweighting of element 1 or underweighting of element 9. The ten elements 1 through 10 are summed in position signal group 1 summing element 907. All position signal groups provide information to position signal selector 1001, which converts the information into a position signal.

As may be appreciated from a review of the stair-stepping arrangement of FIG. 9, the ends of the 76 element array will each have a lone grouping of 5 elements and 5 weights which will normally not be summed with other elements. Various options are available in this edge condition. First, the second set of weighting elements may be omitted and the signal from the pertinent five elements only summed with one position signal group rather than the two used for all other diode/detector elements. Alternately, the two groups of five leftover elements may be compared to one another, but this is less desirable. It is recommended that the edge elements simply be weighted and summed using only a single weighting element, rather than the two weighting elements used by the non-edge groups of diode/detector elements.

Figure 10:
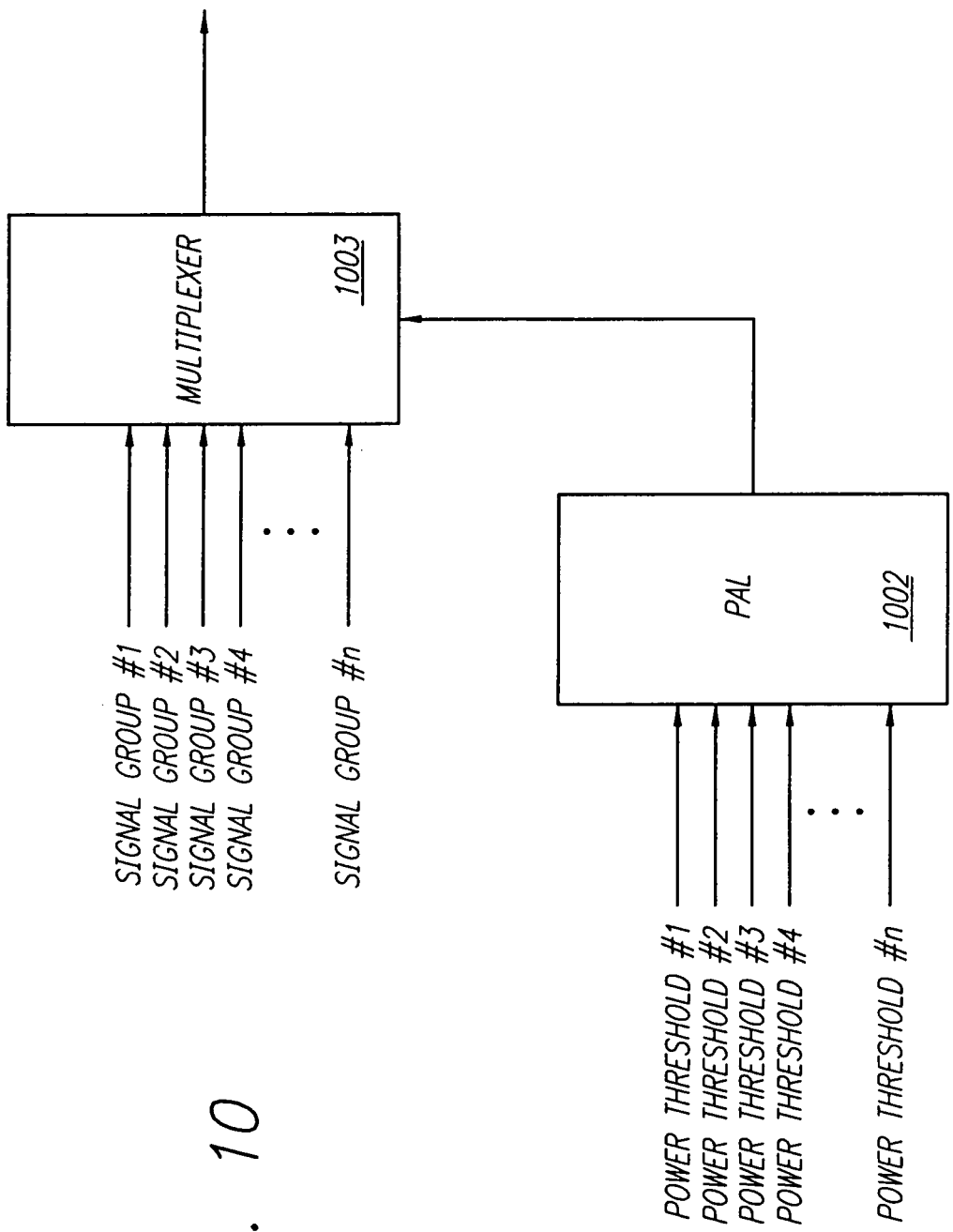
FIG. 10 presents the programmable logic array and multiplexer arrangement used to determine the output signal of the system.

FIG. 10 illustrates passing of data from the various signal groups 1 through n to a multiplexer 1003, which receives a digital signal from programmable array logic (PAL) 1002. From FIG. 10, the system generates a group total detector power for each group in addition to the signal. The power of each group is compared to a given power threshold, and based on the output of these comparisons, the system uses the PAL 1002 to decide which group should be made active. In other words, the PAL determines which group has exceeded the required threshold, passes that group number to the multiplexer 1003, and the multiplexer 1003 only passes the desired group as output. At any given moment, only the group of detectors containing the most power are passed to the system and are used to determine position. The arrangement shown eliminates the electronic and detector noise associated with detectors not containing any signal.

The resultant system provides resolution for various types of anomalies on the wafer surface. Whereas conventional flatness tools had the ability to address problems with bowing/warping, site flatness or thickness variations, and polishing dimples by evaluating relatively large height errors coupled with relatively large lateral dimensions, such tools did not have the ability to detect small height differences and small diameter defects, which required a conventional defect tool. The conventional defect tool could detect particles, scratches, haze, microroughness, and other miscellaneous small extent defects. Certain undesirable surface features had been undetectable using either conventional flatness tools or defect tools, particularly in situations involving device geometries for which relative surface height variations of 100 nanometers or less are significant. The current system provides the ability to address these mid-range concerns, and scanning using the current system takes on the order of minutes rather than several hours to complete.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

We claim:

1. A system for inspecting a specimen, comprising:
   an optical element arrangement for receiving light from a light generating device and imparting light toward said specimen and receiving a retro beam from said specimen;
   a retro beam diversion element for diverting the retro beam from said optical element arrangement;
   a multi-element sensing device for receiving and sensing retro beam position upon diversion from said optical arrangement, said multi-element sensing device comprising a plurality of linearly oriented sensing elements such that said retro beam is received by at least three of said sensing elements; and
   a plurality of weighting elements corresponding to each of said plurality of sensing elements, wherein each of said weighting elements alters a characteristic of an electrical input of said corresponding sensing element based on a distance of said sensing element from a predetermined point on said multi-element device.

2. The system of claim 1, wherein said optical element arrangement comprises an optical isolator.

3. The system of claim 2, wherein said system further comprises:
   a birefringent prism;
   a lensing arrangement for receiving light energy from said birefringent prism;
   at least one mirror, wherein one mirror receives light energy from said optical isolator; and
   a half wave plate for receiving light energy from said one mirror and transmitting light energy to said birefringent prism.

4. The system of claim 2, wherein said optical element arrangement further comprises a dark field collection arrangement.

5. The system of claim 1, wherein said optical element arrangement comprises an optical isolator, and said retro beam diversion element diverts light energy received from said optical isolator.

6. The system of claim 1, wherein said retro beam diversion element comprises a beamsplitter.

7. The system of claim 1, wherein said specimen comprises a surface, and wherein said sensing device senses diversion of said retro beam from an expected value and said system further comprises means for mapping a two dimensional x-y representation of the specimen surface based on signals received from said sensing device.

8. The system of claim 1, wherein said optical element arrangement comprises a Nomarski Differential Interference Contrast sensor.

9. The system of claim 8, wherein said Nomarski Differential Interference Contrast sensor divides light received in a single beam into a plurality of beams; and
   wherein said optical element arrangement imparts a plurality of beams onto said specimen.

10. The system of claim 9, wherein the plurality of beams comprises two beams and wherein the system scans the specimen in a direction substantially parallel to a line joining said two beams.

11. The system of claim 1, wherein said sensing device comprises a one dimensional detector array.

12. The system of claim 11, wherein said one dimensional detector array comprises one from the group including a CCD, a position sensitive detector, and a linear diode array.

13. The system of claim 1, wherein said sensing device comprises:
   a plurality of detector elements having exposed ends and predetermined spacing between said detector elements;
   a plurality of electrical connections affixed to said exposed ends of said detector elements; and
   a plurality of preamplifiers, wherein each detector element has a preamplifier associated therewith.

14. The system of claim 13, further comprising:
   a first plurality of weighting elements, each weighting element having a first predetermined weight associated therewith and electrically connected to a preamplifier;
   a second plurality of weighting elements, said second plurality of weighting elements having a second predetermined weight associated therewith and electrically connected to a preamplifier wherein said first predetermined weight differs from said second predetermined weight; and
   a plurality of summing amplifiers for receiving and combining weighted signals from predetermined weighting elements;
   whereby each preamplifier is electrically connected to two weighting elements.

15. The system of claim 14, further comprising:
   programmable array logic for receiving signals from said summing amplifiers and predetermined power thresholds and selecting signals to be transmitted based on said predetermined power thresholds; and a multiplexer for receiving output selection signals from said programmable array logic and transmitting appropriate signals from said summing amplifiers.

16. The system of claim 1, wherein said light generating device comprises a laser.

17. The system of claim 1, wherein light is imparted toward said specimen and said retro beam is received in a orientation substantially normal to said specimen.

18. The system of claim 1, wherein said specimen moves relative to said optical element arrangement.

19. A system for detecting contours on a specimen surface, comprising:

application means for applying light energy to said specimen surface, said application means comprising a light generating device and an optical element arrangement for receiving light from said light generating device and imparting light toward said specimen surface;

detecting means comprising an optical relay for transmitting light energy received from said specimen surface and receiving a retro beam deflected therefrom and transmitting a retro beam toward a multi-element sensing device comprising a plurality of linearly oriented sensing elements such that said retro beam is received by at least three of said sensing elements; and weighting means comprising a plurality of weighting elements corresponding to each of said plurality of linearly oriented sensing elements, wherein each of said weighting elements alters an electrical characteristic of said corresponding sensing element based on a distance of said sensing element from a predetermined point on said multi-element device.

20. The system of claim 19, further comprising:
an optical diversion element;
wherein said sensing elements receive the retro beam diverted by said optical diversion element.

21. The system of claim 20, wherein said sensing elements comprise a linear array of sensors.

22. The system of claim 19, further comprising: summing means for summing information received from said weighting means.

23. The system of claim 22, further comprising programmable array logic and a multiplexer, wherein said programmable array logic determines signals based on predetermined threshold exceedance and initiates any determined signal via said multiplexer.

24. The system of claim 19, wherein said detecting means have the ability to detect surface variations having relative surface height variations of less than approximately 1000 nanometers and greater than approximately 1.0 nanometer.

25. The system of claim 24, wherein said detecting means have the ability to detect surface variations having relative surface height variations of less than approximately 1000 nanometers and greater than approximately 0.1 nanometer.

26. A method for inspecting a specimen, comprising:

providing light energy to said specimen via an arrangement of optical elements, thereby creating a retro beam reflected from said specimen;

passing said retro beam back through said arrangement of optical elements;

providing said retro beam to a multi-element sensing device, said retro beam having an expected deflection in a substantially predetermined direction and said multi-element sensing device comprising a plurality of linearly oriented sensing elements such that said retro beam is received by at least three of said sensing elements, each of said sensing elements producing an electrical output in response to sensing a portion of said retro beam; and altering a characteristic of said electrical output according to a weighting element corresponding to a distance of said plurality of sensing elements from a predetermined point on said multi-element sensing device;

wherein said sensing device senses movement of the retro beam corresponding to anomalies on said specimen.

27. The method of claim 26, wherein said optical element arrangement comprises:
a birefringent prism; and
a lensing arrangement, said lensing arrangement comprising a plurality of optical lenses.

28. The method of claim 27, wherein said optical arrangement further comprises:
an optical isolator;
a half wave plate; and
at least one mirror.

29. The method of claim 26, wherein said optical element arrangement comprises an optical isolator, and said retro beam providing step diverts light energy received from said optical isolator.

30. The method of claim 26, wherein said retro beam providing step comprises diverting the retro beam via a beamsplitter.

31. The method of claim 26, wherein said optical element arrangement comprises a bright field scanning Nomarski Differential Interference Contrast sensor.

32. The method of claim 31, wherein said bright field scanning Nomarski Differential Interference Contrast sensor measures deviation along a direction substantially perpendicular to an optical lever.

33. The method of claim 26, wherein said sensing device comprises:
a plurality of detector elements having exposed ends and predetermined spacing between said elements;
a plurality of electrical connections affixed to said exposed ends of said detector elements; and
a plurality of preamplifiers, wherein each element has a preamplifier associated therewith.

34. The method of claim 26, wherein said optical element arrangement comprises a bright field scanning Nomarski Differential Interference Contrast sensor.

35. The method of claim 34, wherein bright field scanning Nomarski Differential Interference Contrast sensor measures deviation along a direction substantially perpendicular to the orientation of beams created thereby.

36. The method of claim 26, wherein said light energy is provided to said specimen in a substantially normal orientation.

37. The method of claim 26, further comprising moving said specimen relative to said arrangement of optical elements.

38. A method for detecting contours on a specimen surface, comprising:

applying light energy to said specimen surface, said light application comprising generating light using a light generating device and receiving light from said light generating device and imparting light toward said specimen surface;

detecting surface variations, said detecting comprising transmitting light energy received from said specimen surface, receiving a retro beam deflected therefrom and transmitting said retro beam toward a multi-element sensing device comprising a plurality of linearly oriented sensing elements such that said retro beam is received by at least three of said sensing elements; and altering an electrical characteristic of said corresponding sensing element based on a distance of said sensing element from a predetermined point on said multi-element device.

39. The method of claim 38, further comprising the steps of:

optically diverting light energy after said applying step; and detecting movement of said retro beam by receiving the retro beam diverted by said optical diversion step.

40. The method of claim 38, further comprising the steps of weighting and summing information received from said detecting step.

* * * * *